United States Patent [19]

Cosgrove et al.

[11] Patent Number: 5,643,226

[45] Date of Patent: Jul. 1, 1997

[54] LOW VELOCITY AORTIC CANNULA

[75] Inventors: Delos M. Cosgrove, Hunting Valley; J. Frederick Cornhill, Worthington, both of Ohio; Christopher M. Boykin, Athens, Tex.; Nelson L. Huldin, Pittsfield; William G. O'Neill, Ann Arbor, both of Mich.

[73] Assignees: Minnesota Mining and Manufacturing, St. Paul, Minn.; The Cleveland Clinic Foundation, Cleveland, Ohio

[21] Appl. No.: 319,374

[22] Filed: Oct. 6, 1994

Related U.S. Application Data

[63] Continuation-in-part of Ser. No. 21,811, Feb. 24, 1993, Pat. No. 5,354,288.

[51] Int. Cl.$^6$ .................................................. A61M 25/00
[52] U.S. Cl. ...................... 604/264; 604/53; 604/280; 604/93
[58] Field of Search ................................. 604/30, 31, 39, 604/44, 46, 53, 264, 272–275, 280, 93; 600/15–17

[56] References Cited

U.S. PATENT DOCUMENTS

| | | |
|---|---|---|
| 275,405 | 4/1883 | Parker . |
| 609,280 | 8/1898 | King . |
| 611,454 | 9/1898 | Longden . |
| 829,952 | 9/1906 | Dean ........................ 128/278 |
| 2,356,659 | 8/1944 | da Paiva Aguiar ........... 128/278 |
| 2,393,728 | 1/1946 | de P. Aguiar ............... 128/276 |
| 2,854,983 | 10/1958 | Baskin ...................... 128/349 |
| 2,862,498 | 12/1958 | Weekes ..................... 128/351 |
| 3,108,595 | 10/1963 | Overment .................. 128/350 |
| 3,397,699 | 8/1968 | Kohl ........................ 128/349 |
| 3,568,659 | 3/1971 | Karnegis ................... 128/1 |
| 3,605,750 | 9/1971 | Sheridan et al. ........... 128/348 |
| 3,799,172 | 3/1974 | Szpur ....................... 128/349 |
| 3,938,530 | 2/1976 | Santomieri ................. 128/349 |
| 3,955,573 | 5/1976 | Hansen et al. .............. 128/276 |
| 3,964,484 | 6/1976 | Reynolds et al. ........... 128/276 |
| 4,297,115 | 10/1981 | Johnson, Jr. ............... 55/302 |
| 4,321,920 | 3/1982 | Gillig ...................... 128/239 |
| 4,375,816 | 3/1983 | Labianca .................... 604/8 |
| 4,437,856 | 3/1984 | Valli ........................ 604/29 |

(List continued on next page.)

OTHER PUBLICATIONS

Advertising flyer for "Argyle ® Lighthouse Tip Vena Caval Catheter", by Sherwood Medical Company, dated 1985.

Charles C. Reed, Diane K. Clark, Chapter 19, "Cannulation", Chapter 23 Myocardial Protection, *Cardiopulmonary Perfusion*, Texas Medical Press, Inc., Houston, Texas, 1975.

"Atheroembolism From The Ascending Aorta", *The Journal of Thoracic and Cardiovascular Surgery*, C. Blauth et al., 1104–1111.

*Primary Examiner*—Robert A. Hafer
*Assistant Examiner*—Chalin Smith
*Attorney, Agent, or Firm*—Armstrong, Teasdale, Schlafly & Davis

[57] ABSTRACT

An improved aortic cannula having a sidewall with a proximal end, a distal end, and a lumen therebetween for conducting blood, the distal end being adapted for insertion into the aorta during heart surgery to provide blood to the aorta. The cannula has a cap substantially blocking axial flow through the distal end of the lumen. There are a plurality of outlet openings in the sidewall of the cannula adjacent the distal end. The distal end of the lumen is flush with or preferably distally beyond the distal ends of the outlet openings. The aortic cannula may have a bend therein, as is known in the art, in which case the outlet openings on the outside side of the bend are smaller than the outlet openings on the inside side of the bend, to reduce disparity in the flow that would otherwise be caused by the bend, substantially equalizing flow through the openings. According to the method of this invention, an opening is made in the aorta of the patient; the distal end of the cannula is inserted into the opening in the aorta; and blood flow through the cannula is initiated to provide blood to the aorta without jetting.

32 Claims, 3 Drawing Sheets

U.S. PATENT DOCUMENTS

| | | | |
|---|---|---|---|
| 4,522,195 | 6/1985 | Schiff | 128/1 |
| 4,535,757 | 8/1985 | Webster, Jr. | 128/1 |
| 4,575,371 | 3/1986 | Nordqvist et al. | 604/96 |
| 4,580,568 | 4/1986 | Gianturco | 128/345 |
| 4,617,019 | 10/1986 | Fecht et al. | 604/280 |
| 4,643,712 | 2/1987 | Kulik et al. | 604/4 |
| 4,655,745 | 4/1987 | Corbett | 604/49 |
| 4,680,029 | 7/1987 | Ranford et al. | 604/280 |
| 4,693,243 | 9/1987 | Buras | 128/207 |
| 4,787,882 | 11/1988 | Claren | 604/4 |
| 4,795,439 | 1/1989 | Guest | 604/43 |
| 4,795,446 | 1/1989 | Fecht | 604/264 |
| 4,802,819 | 2/1989 | Bevington et al. | 415/199.3 |
| 4,813,935 | 3/1989 | Haber et al. | 604/99 |
| 4,863,441 | 9/1989 | Lindsay et al. | 604/280 |
| 4,921,478 | 5/1990 | Solano et al. | 604/53 |
| 4,966,585 | 10/1990 | Gangemi | 604/131 |
| 5,021,044 | 6/1991 | Sharkawy | 604/53 |
| 5,084,033 | 1/1992 | O'Neill et al. | 604/264 |
| 5,300,022 | 4/1994 | Klapper et al. | 604/35 |

LOW VELOCITY AORTIC CANNULA

CROSS REFERENCE TO RELATED APPLICATION

This application is a continuation-in-part of U.S. patent application Ser. No. 08/021,811, filed Feb. 24, 1993 now U.S. Pat. No. 5,354,288.

FIELD OF THE INVENTION

This invention relates to a low velocity aortic cannula for use during heart surgery, and a method of delivering blood to the aorta using a low velocity aortic cannula.

BACKGROUND AND SUMMARY OF THE INVENTION

Aortic cannulas are used to return blood to the aorta while the heart is by-passed during heart surgery. These cannulas are purposely made with small diameters (typically six to eight millimeters, but even smaller for pediatric applications) to minimize the disruption to the aorta, which in many heart surgery patients have advanced complex atherosclerotic lesions with adherent blood thrombi. The flow velocities through these small diameter cannula must be very high in order to maintain a satisfactory blood flow rate of about five to seven liters per minute. In at least some styles of conventional aortic cannula now in use, this high velocity resulted in "jet" flow emanating from the distal end of the cannula, which acted as a nozzle. It is believed that the force of this narrow jet stream may dislodge atheromatous material and/or adherent thrombi from the walls of the aorta, causing embolisms. As surgical equipment and techniques improve, making heart surgery available to older and more seriously ill patients, thrombo-atheroembolisms affect an increasing number of patients due to the increasing extent of atherosclerosis with age.

The size of aortic cannula may be constrained by the constricted size of the aorta of the typical heart surgery patient. Moreover, the ability to diffuse flow is restricted by the fragility of the blood, which is easily damaged by the shear stresses associated with turbulence.

The aortic cannulas of the present invention are adapted to provide high volume flow at relatively lower flow velocities than the conventional aortic cannulas presently available, thereby reducing the jet flow and consequently reducing the incidence of thrombo-atheroembolisms. Generally aortic cannulas constructed according to the principles of this invention have a sidewall with a proximal end, a distal end, and a lumen therebetween for conducting blood. The cannula also has a distal end cap that blocks substantially all of the axial flow through the distal end of the cannula. There are a plurality of outlet openings in the sidewall of cannula, adjacent the distal end, to maintain flow volume of blood through the cannula. The distal end of the lumen is at least flush with the distal ends of the outlet openings, and preferably the lumen extends distally beyond the outlet openings.

The distal end of the lumen is configured to cause the flow through the outlet openings to extend more radially outwardly, with a concave, flat, or convex surface. In the preferred embodiment, the distal end of the lumen preferably has a centrally located land projecting proximally from the distal end. The surface of this land is generally a segment of a sphere. While it is preferable that the distal end of the lumen have this land, it is not essential, and desirable blood flow patterns without significant hemolysis can be achieved so long as the distal end of the lumen is at least flush with the distal ends of the outlet openings, but preferably distal end of the lumen extends between about 0.005 inches (0.127 mm) and about 0.200 inches (5.08 mm) distally beyond the distal end of the outlet openings, and more preferably about 0.090 inches (2.29 mm) beyond the distal end of the outlet openings.

The aortic cannula of the present invention creates a conical sheet flow, when viewed from the side, with a large cone angle such that the bulk of the flow from the cannula is more radial than axial. When viewed axially, the flow has a generally clover leaf shape, with a lobe corresponding to each outlet opening. This diffuse flow reduces the high velocity jetting that can occur with some aortic cannulas, while maintaining an adequate flow rate and minimizing damage to the blood.

These and other features and advantages will be in part apparent and in part pointed out hereinafter.

BRIEF DESCRIPTION OF THE DRAWINGS

Corresponding reference numerals indicate corresponding parts throughout the several views of the drawings.

DETAILED DESCRIPTION OF THE PREFERRED EMBODIMENTS

Figures 1, 2, 3, 5, 6B:
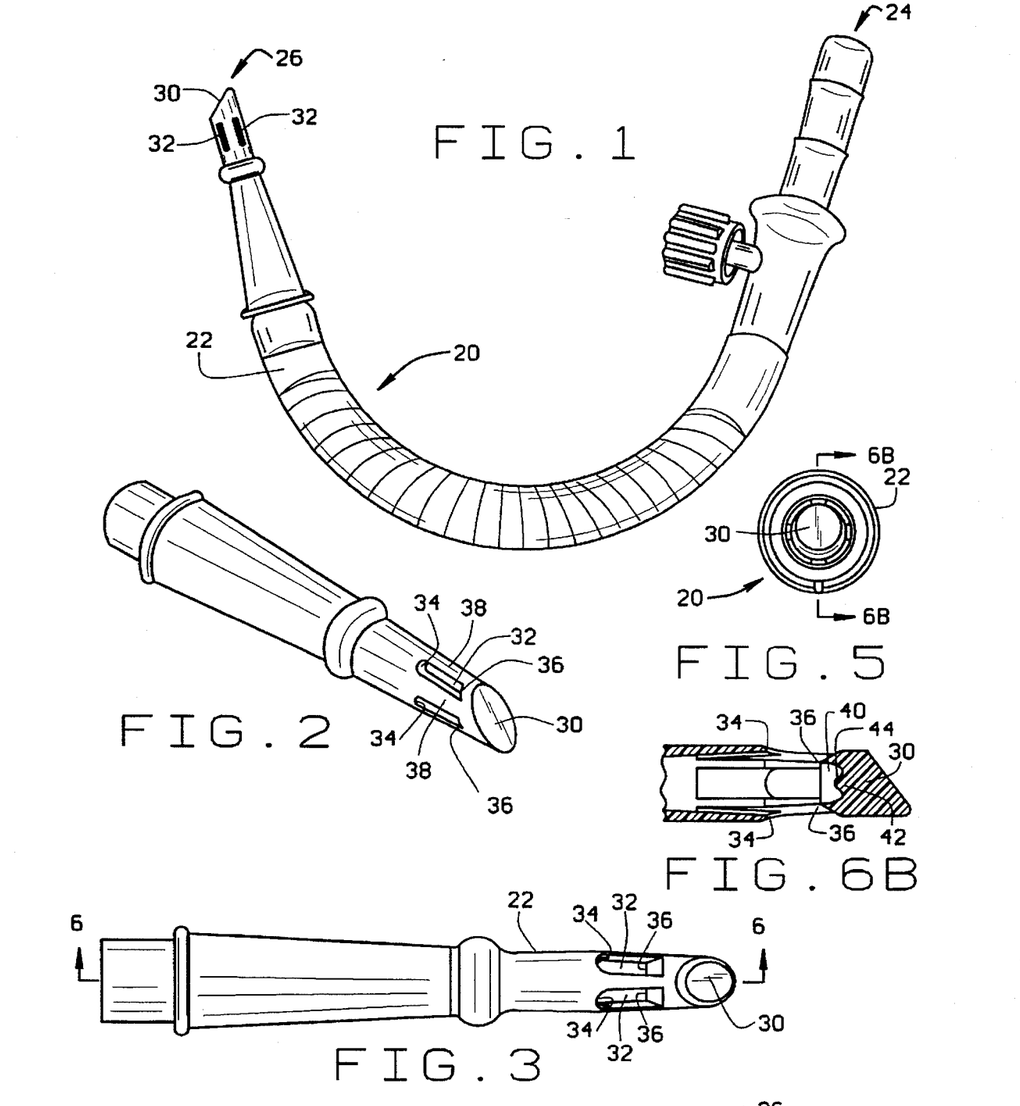
FIG. 1 is a side elevation view of a first embodiment of an aortic cannula constructed according to the principles of this invention.
FIG. 2 is a perspective view of the tip of the aortic cannula of the first embodiment.
FIG. 3 is a top plan view of the tip of the aortic cannula of the first embodiment.
FIG. 5 is an end elevation view of the tip of the aortic cannula of the first embodiment.
FIG. 6B is a side view of the tip of the aortic cannula of the first embodiment shown in FIG. 6.
Figure 4:
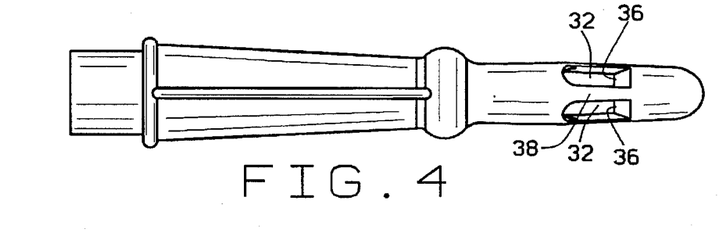
FIG. 4 is a bottom plan view of the tip of the aortic cannula of the first embodiment.

A first embodiment of an aortic cannula constructed according to the principles of this invention is indicated generally as 20 in FIG. 1. The aortic cannula 20 comprises a generally tubular sidewall 22 having a proximal end 24 and a distal end 26, with a lumen 28 extending therebetween. As shown in FIG. 1, the cannula tapers toward the distal end so that the distal end has a diameter of between about 6 mm and 8 mm, to fit in the aorta of the patient. As shown in FIG. 2, the distal end 26 of the cannula 20 is substantially closed with an end cap 30. The cap 30 preferably has a beveled configuration resembling a conventional aortic cannula tip, as shown in the Figures. The cap may alternatively have a rounded hemispherical shape or a rounded, conical shape, as is known in the art. The cap 30 is preferably molded in one piece with the cannula.

A plurality of outlet openings 32 are formed in the sidewall of the cannula 20, adjacent the distal end 26. These openings 32 preferably have an arched configuration, with the curved portion 34 of each arch oriented toward the proximal end 24 of the cannula, i.e., oriented in the upstream direction. The distal ends 36 of the openings preferably have a beveled configuration, sloping generally outwardly in the distal axial direction, as shown best in FIG. 6B. There are preferably four openings 32, equally spaced around the circumference of the distal end 26 of the cannula. However, there could be fewer or more openings 32, if desired. The total area of the openings 32 is preferably greater than the area of the distal end opening in a conventional aortic cannula of the same diameter. The length of the openings 32 is preferably about 0.275 inches (7 mm) to about 0.300 inches (7.62 mm), and the width of the openings (in this preferred embodiment) is about 0.130 inches (3.30 mm). The openings are sufficiently large to allow sufficient flow through the cannula to avoid large pressure drops, and to achieve the desired flow configuration explained below. The openings 32 are separated by struts 38, which are preferably thicker than the normal wall thickness of the cannula so that the struts have sufficient strength to hold the cap 30.

Figure 6:
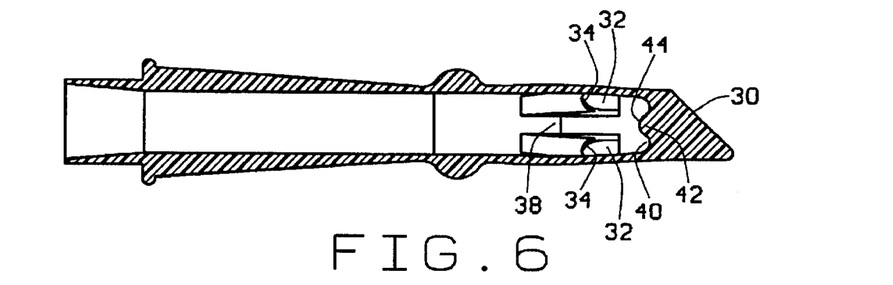
FIG. 6 is a longitudinal cross-sectional view of the tip of the aortic cannula of the first embodiment taken along the plane of line 6—6 in FIG. 3.

The cap 30 substantially blocks axial flow from the cannula, although because of the draft in the cannula tip (as a result of molding), anywhere from zero to about five percent of the area of the outlet openings 32 may not be blocked in the axial direction (see FIG. 5). The lumen 28 extends distally so that the distal end of the lumen is at least flush with the distal ends of the outlet openings 32, and as best show in FIGS. 6 and 7, the lumen preferably extends beyond the distal ends of the openings 32. The distal end 40 of the lumen 28 is preferably between about 0.005 and about 0.200 inches distally beyond the distal ends of the outlet openings, and more preferably between about 0.040 and 0.050 inches beyond the distal ends of the outlet openings.

The distal end 40 of the lumen can have a concave, flat, or convex configuration. Preferably the distal end 40 has a smooth, rounded configuration. In this preferred embodiment there is a raised land 42 in the center of the distal end 40 of the lumen 28. The land 42 projects proximally such that proximal end 44 of the land 42 is still distal (or downstream) of the distal ends of the outlet openings 32. In this preferred embodiment the land preferably projects about 0.030 inches (0.762 mm) such that the land is still about 0.060 inches (1.52 mm) distal of the distal ends of the outlet openings. The land 42 has a smooth, round configuration, preferably the shape of the surface of a segment of a sphere.

The inventors have found that when the distal end 40 of the lumen 28 is at least flush with the distal ends of the outlet openings, the flow through the outlet openings is altered, such that the direction of flow becomes more radial and less axial. This affect becomes more pronounced when the distal end 40 of the lumen is distally beyond the distal ends of the outlet openings, preferably at least about 0.005 inches (0.127 mm), and most preferably about 0.090 inches (2.29 mm). The effect is still noted when the distal end 40 of the lumen is as much as 0.200 inches (5.08 mm) beyond the distal ends of the outlet openings.

When viewed from the side, the flow from the cannula 20 is generally shaped like a hollow cone, with a large cone angle such that the direction of the bulk of the flow is more radial than axial. See FIG. 8. When viewed axially, the flow has a somewhat clover-leaf shape with a lobe corresponding to each outlet opening 32. See FIG. 9.

The inventors believe that closed distal end 40 of the lumen 28 creates a back flow which, when it encounters the main flow in the lumen, diverts that flow radially outwardly through the outlet openings 32. Surprisingly, this creates very little, if any, hemolysis. The inventors attribute the low level of hemolysis to the fact that the blood flow is diverted by another blood flow, rather than a solid obstacle, such as a diffuser.

As blood flows through the cannula 20 and reaches the distal end 26, the cannula imparts a radially outward component to the flow. The diffused flow is thus urged out through the openings 32, with a reduced velocity, because of the greater area of the openings 32. The configuration of the cannula with the lumen extending distally of the distal end of the outlet openings diverts the flow radially outwardly through the opening with relatively low turbulence, and relatively little hemolysis.

Figure 8:
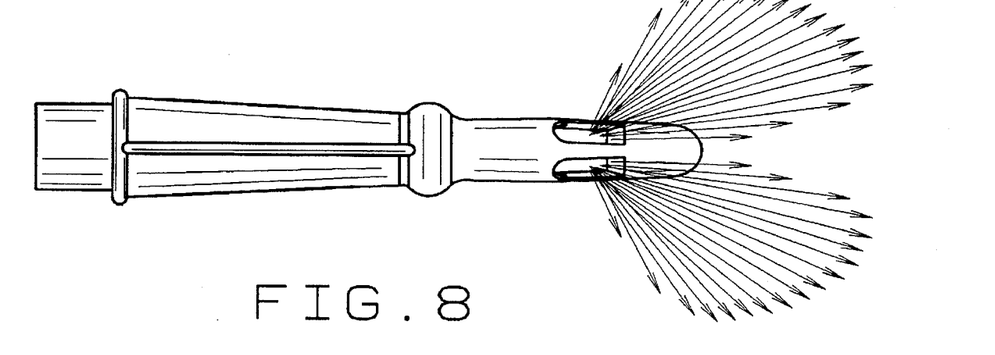
FIG. 8 is a bottom plan view of the tip of the aortic cannula of the first embodiment, with arrows showing the direction and contour of flow from the cannula.
Figure 9:
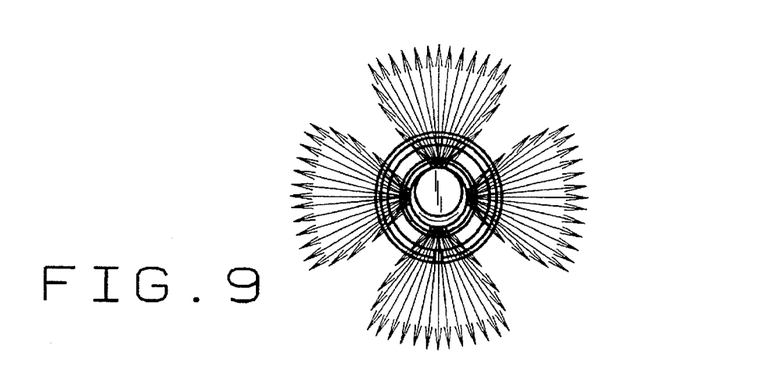
FIG. 9 is an end elevation view of the tip of the aortic cannula of the first embodiment, with arrows showing the direction and contour of the flow.

As shown in FIGS. 8 and 9, the cannula splays out the flow, forming an "umbrella" pattern that quickly establishes a stable flow within the aorta, reducing high velocity jetting and creating a more uniform flow velocity across the diameter of the aorta.

Figure 7:
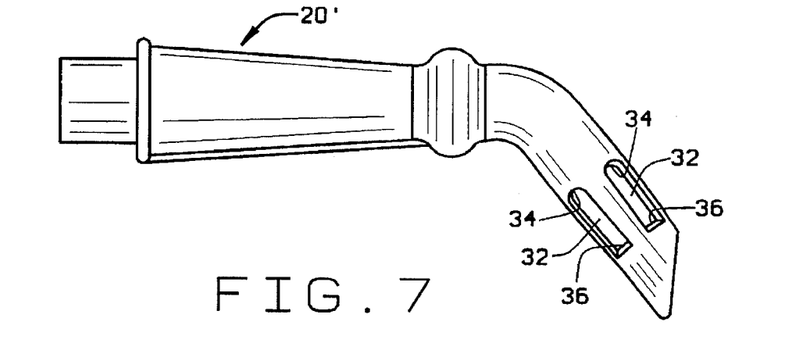
FIG. 7 is a side elevation view of a second embodiment of an aortic cannula constructed according to the principles of this invention.

A second embodiment of an aortic cannula constructed according to the principles of this invention is indicated generally as 20' in FIG. 7. Cannula 20' is identical to cannula 20, described above, except that the distal end of the cannula is bent as shown. This bent configuration is sometimes easier to insert into and/or maintain within the aorta.

The Inventors have discovered that in cannula constructed according to the second embodiment of this invention, the flow through the windows on the outside side of the bend is greater than the flow through equally sized windows on the inside side of the bend. The inventors have solved this problem by making the windows on the outside side of the bend smaller than the windows on the inside side of the bend. A preferred way of accomplishing this to move the distal end 36 of the windows 32 on the outside side of the bend proximally, so that the length of the windows on the outside side of the bends is less than the length of the windows on the inside side of the bend. Thus, for example, in the preferred embodiment shown in FIG. 10 if the windows were 0.325 inches long on the inside side of the bend, the windows on the outside side of the bend would be only 0.300 inches long with the distal end 36o of the windows on the outside side of the bend located 0.025 inches proximally of the distal ends 36i of the windows on the inside side of the bend.

Figure 10:
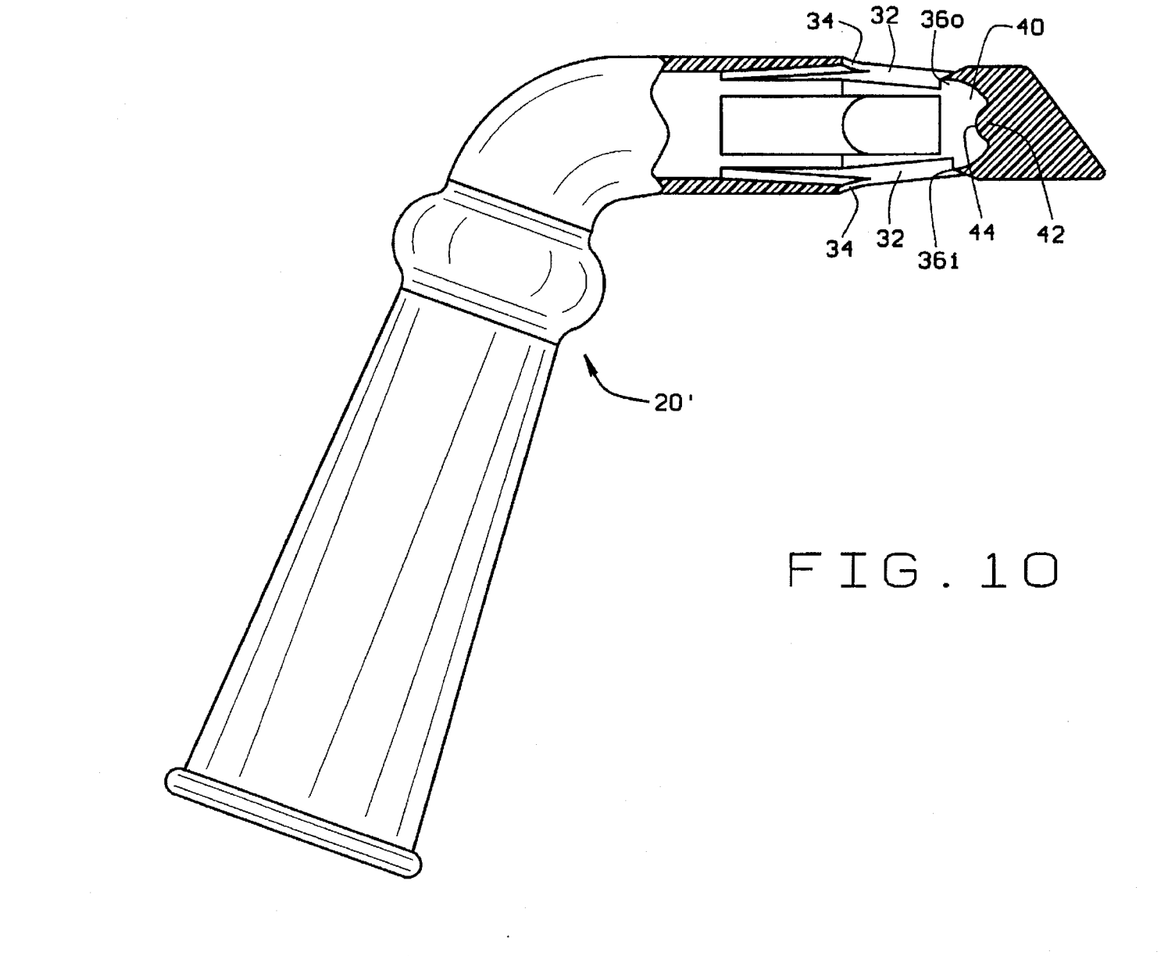
FIG. 10 is a longitudinal cross-sectional view of an alternate construction of a second embodiment of this invention.

The appropriate size of the windows on the outside side of the bend, and the appropriate position for the distal ends of the windows can be determined empirically, or by finite element analysis, to substantially equalize the flows and the pressure drops to obtain a more uniform flow distribution through the windows.

OPERATION

In operation, an opening is made into the aorta and the distal end of the cannula 20 or 20' is inserted into the aorta. The beveled configuration of cap 30 facilitates the insertion of cannula 20 into the aorta. When the cannula 20 or 20' is secured in place, blood flow is initiated. Blood flows through the lumen 28 and out the outlet openings 32 at the distal end 26 of the cannula.

The blood flow encounters the rounded, blunt distal end 40 of the lumen which redirects the flow axially in the proximal direction. When the axial distal flow encounters the rebounding proximal flow, the bulk of the distal flow is diverted radially outwardly through the outlet openings in a sheet-like cone. Thus, rather than a jetting, axial flow experienced with conventional aortic cannula, the cannula 20 and 20' provide a diffused flow that more quickly establishes a stable, more uniform velocity blood flow in the aorta. The flow properties of the blood are such that the cannula creates an "umbrella" flow pattern, as shown in FIGS. 8 and 9, that more quickly establishes a uniform flow in the aorta.

The cannulas 20 and 20' of this invention thus reduce maximum flow velocity, the variation in flow velocity, and the maximum flow force, while maintaining the overall flow rate. These reductions are believed to be significant in the reduction of thrombo-atheroembolisms, and other possible complications of heart surgery.

The following chart illustrates the reduction achieved in peak velocity of cannula constructed according to the principles of this invention. Measurements were made in a model human aorta of the peak flow speed for each of the aortic cannulas listed. The location of the peak flow speed varied from 0 to 12 mm from the cannula tip.

| CANNULA | PEAK VELOCITY (cm/s) |
| --- | --- |
| Cannula 20 or 20' | 223.9 |
| RMI | 668 |
| Argyle | 570 |
| Bard | 816 |

The chart illustrates that peak flow speed (in cm/s) is lowered for the cannula constructed accordingly to this invention. The inventors believe that this reduced flow speed corresponds to a reduction in the ability of the flow to dislodge arthramatous material from the walls of the aorta.

As various changes could be made in the above constructions without departing from the scope of the invention, it is intended that all matter contained in the above description or shown in the accompanying drawings shall be interpreted as illustrative and not in a limiting sense.

What is claimed is:

1. An improved aortic cannula having a sidewall with a proximal end, a distal end, and a lumen therebetween for conducting blood, the distal end being adapted for insertion into the aorta during heart surgery to provide blood to the aorta the improvement comprising:
   a cap substantially blocking axial flow through the distal end of the lumen;
   a plurality of arch-shaped outlet openings in the sidewall of the cannula adjacent the distal end, each of the outlet openings having an arcuate proximal end, and a straight distal end, the distal end having a beveled configuration sloping generally outwardly in the distal axial direction; and
   the distal end of the lumen being located flush with or distally beyond the distal ends of the outlet openings.

2. The improved aortic cannula according to claim 1 wherein the cannula has a bend therein proximal to the outlet openings.

3. The improved aortic cannula according to claim 1 wherein the portion of the sidewall of the lumen immediately proximal to the outlet openings slopes outwardly in the distal axial direction.

4. The improved aortic cannula according to claim 1 wherein the distal end of the lumen extends distally beyond the distal ends of the outlet openings.

5. The improved aortic cannula according to claim 4 further comprising a raised land projecting proximally from the distal end of the lumen.

6. The improved aortic cannula according to claim 4 wherein the surface of the land is shaped like the surface of a segment of a sphere.

7. The improved aortic cannula according to claim 5 wherein the land extends proximally about 0.030 inches (0.762 mm) from the distal end of the lumen.

8. An improved aortic cannula having a sidewall with a proximal end, a distal end, and a lumen therebetween for conducting blood, the distal end being adapted for insertion into the aorta during heart surgery to provide blood to the aorta, the improvement comprising:
   a cap substantially blocking axial flow through the distal end of the lumen;
   a plurality of outlet openings in the sidewall of the cannula adjacent the distal end; and
   the distal end of the lumen being located between about 0.005 inches (0.127 mm) and about 0.200 inches (5.08 mm) distally beyond the distal ends of the outlet openings.

9. The improved aortic cannula according to claim 8 wherein the distal end of the lumen is located about 0.090 inches (2.29 mm) distally beyond the distal ends of the outlet openings.

10. An improved aortic cannula having a sidewall with a proximal end, a distal end, and a lumen therebetween for conducting blood, the distal end being adapted for insertion into the aorta during heart surgery to provide blood to the aorta, the improvement comprising:
    a cap substantially blocking axial flow through the distal end of the lumen;
    a plurality of outlet openings in the sidewall of the cannula adjacent the distal end, the distal end of the lumen being located distally beyond the distal ends of the outlet openings; and
    a raised land projecting proximally from the distal end of the lumen, such that the proximal end of the land is distal to the distal ends of the outlet openings.

11. The improved aortic cannula according to claim 10 wherein the proximal ends of the outlet openings have an arcuate shape.

12. An improved aortic cannula having a sidewall with a proximal end, a distal end, and a lumen therebetween for conducting blood, the distal end being adapted for insertion into the aorta during heart surgery to provide blood to the aorta, the improvement comprising:
    a cap substantially blocking axial flow through the distal end of the lumen;
    a plurality of outlet openings in the sidewall of the cannula adjacent the distal end, the distal ends of the outlet openings having a beveled configuration, sloping generally outwardly in the distal axial direction, the distal end of the lumen being located distally beyond the distal ends of the outlet openings; and
    a raised land projecting proximally from the distal end of the lumen, such that the proximal end of the land is distal to the distal ends of the outlet openings.

13. An improved aortic cannula having a sidewall with a proximal end, a distal end, and a lumen therebetween for conducting blood, the distal end being adapted for insertion into the aorta during heart surgery to provide blood to the aorta, the improvement comprising:
    a cap substantially blocking axial flow through the distal end of the lumen;

a plurality of outlet openings in the sidewall of the cannula adjacent the distal end; the distal end of the lumen being located flush with, or distally beyond the distal ends of the outlet openings;

the cannula having a bend therein proximal to the outlet openings, and at least some of the outlet openings on the outside side of the bend being smaller than at least some of the openings on the inside side of the bend to reduce the disparity in flow between openings on the inside and outside sides of the bend that would otherwise be caused by the bend.

14. An improved aortic cannula having a sidewall with a proximal end, a distal end, and a lumen therebetween for conducting blood, the distal end being adapted for insertion into the aorta during heart surgery to provide blood to the aorta, the improvement comprising:

a cap substantially blocking axial flow through the distal end of the lumen;

a plurality of outlet openings in the sidewall of the cannula adjacent the distal end;

the distal end of the lumen being located flush with, or distally beyond the distal ends of the outlet openings; and the cannula having a bend therein proximal to the outlet openings, wherein at least some of the outlet openings on the outside side of the bend are smaller than at least some of the openings on the inside side of the bend to substantially equalize flow through the openings.

15. A method of providing blood to the aorta of a patient, the method comprising the steps of:

making an opening in the aorta of the patient;

providing a cannula having sidewall with a proximal end, a distal end, and a lumen therebetween for conducting blood, the distal end being adapted for insertion into the aorta during heart surgery to provide blood to the aorta; a cap substantially blocking axial flow through the distal end of the lumen; and a plurality of arch-shaped outlet openings in the sidewall of the cannula adjacent the distal end; each of the outlet openings having an arcuate proximal end and a beveled configuration sloping generally outwardly in the distal direction; the distal end of the lumen being located flush with or distally beyond the distal ends of the outlet openings;

inserting the distal end of the cannula into the opening in the aorta; and initiating blood flow through the cannula to provide blood to the aorta.

16. The method according to claim 15 wherein the portion of the sidewall of the lumen immediately distal to the outlet openings slopes outwardly in the distal axial direction.

17. The method according to claim 15 wherein the distal end of the lumen extends distally beyond the distal ends of the outlet openings.

18. The method according to claim 17 wherein the distal end of the lumen is located between about 0.005 inches (0.127 mm) and about 0.200 inches (5.08 mm) distally beyond the distal ends of the outlet openings.

19. The method according to claim 17 wherein the distal end of the lumen is located about 0.090 inches (2.29 mm) distally beyond the distal ends of the outlet openings.

20. The method according to claim 17 wherein the cannula has a bend therein proximal to the outlet openings.

21. The method according to claim 17 wherein the aortic cannula further comprises a raised land projecting proximally from the distal end of the lumen.

22. The method according to claim 21 wherein the surface of the land is shaped like the surface of a segment of a sphere.

23. The method according to claim 21 wherein the land extends proximally about 0.030 inches (0.762 mm) from the distal end of the lumen.

24. A method of providing blood to the aorta of a patient, the method comprising the steps of:

making an opening in the aorta of the patient;

providing a cannula having a sidewall with a proximal end, a distal end, and a lumen therebetween for conducting blood, the distal end being adapted for insertion into the aorta during heart surgery to provide blood to the aorta; a cap substantially blocking axial flow through the distal end of the lumen; and a plurality of outlet openings in the sidewall of the cannula adjacent the distal end; the distal end of the lumen being located flush with, or distally beyond the distal ends of the outlet openings; and a raised land projecting proximally from the distal end of the lumen, such that the proximal end of the land is distal to the distal ends of the outlet openings;

inserting the distal end of the cannula into the opening in the aorta; and initiating blood flow through the cannula to provide blood to the aorta.

25. The method according to claim 24 wherein the proximal ends of the outlet openings have an arcuate shape.

26. The method according to claim 24 wherein the distal ends of the outlet openings have a beveled configuration, sloping generally outwardly in the distal axial direction.

27. A method of providing blood to the aorta of a patient, the method comprising the steps of:

making an opening in the aorta of the patient;

providing a cannula having a sidewall with a proximal end, a distal end, and a lumen therebetween for conducting blood, the distal end being adapted for insertion into the aorta during heart surgery to provide blood to the aorta; a cap substantially blocking axial flow through the distal end of the lumen; and a plurality of outlet openings in the sidewall of the cannula adjacent the distal end; the distal end of the lumen being located flush with or distally beyond the distal ends of the outlet openings; the cannula having a bend therein proximal to the outlet openings at least some of the outlet openings on the outside side of the bend being smaller than at least some of the openings on the inside side of the bend to substantially equalize the flow through the openings;

inserting the distal end of the cannula into the opening in the aorta; and initiating blood flow through the cannula to provide blood to the aorta.

28. The method according to claim 27 wherein the distal end of the lumen is distal of the distal ends of the openings in the sidewall.

29. A method of providing fluid to the aorta of a patient comprising the steps of making an opening in the aorta of the patient; inserting the distal end of the aortic cannula through the opening into the aorta, the cannula having a lumen with a closed distal end, and a plurality of circumferentially-spaced openings in the sidewall of the cannula, providing fluid under pressure to the lumen the closed distal end of the lumen and the side openings cooperating to form a hollow sheet-like conical flow of fluid from the cannula into the aorta.

30. The method according to claim 29 wherein there is a raised land projecting proximally from the distal end of the lumen, the proximal surface of the land being distal of the distal ends of the openings in the sidewall.

31. A method of providing blood to the aorta of a patient, the method comprising the steps of:

making an opening in the aorta of the patient;

providing a cannula having a sidewall with a proximal end, a distal end, and a lumen therebetween for conducting blood, the distal end being adapted for insertion into the aorta during heart surgery to provide blood to the aorta; a cap substantially blocking axial flow through the distal end of the lumen; and a plurality of outlet openings in the sidewall of the cannula adjacent the distal end; the distal end of the lumen being located flush with or distally beyond the distal ends of the outlet openings; the cannula having a bend therein proximal to the outlet openings at least some of the outlet openings on the outside side of the bend being smaller than at least some of the openings on the inside side of the bend to reduce the disparity in flow between openings on the inside and outside sides of the bend that would otherwise be caused by the bend;

inserting the distal end of the cannula into the opening in the aorta; and initiating blood flow through the cannula to provide blood to the aorta.

32. A method of providing fluid to the aorta of a patient comprising the steps of making an opening in the aorta of the patient; inserting the distal end of the aortic cannula through the opening into the aorta, the cannula having a lumen with a closed distal end, and a plurality of openings in the sidewall of the cannula, the openings being evenly spaced around the circumference of cannula tip; providing fluid under pressure to the lumen the closed distal end of the lumen and the side openings cooperating to form a hollow sheet-like conical flow of fluid from the cannula into the aorta, each of the openings generating a lobe forming the hollow sheet like conical flow.

* * * * *

UNITED STATES PATENT AND TRADEMARK OFFICE
CERTIFICATE OF CORRECTION

PATENT NO : 5,643,226
DATED : July 1, 1997
INVENTOR(S): Delos M. Cosgrove, et al.

It is certified that error appears in the above-identified patent and that said Letters Patent is hereby corrected as shown below:

<u>IN THE CLAIMS</u>:

Column 6, line 4, change "4" to --5--.

Signed and Sealed this

Seventh Day of April, 1998

*Attest:*

BRUCE LEHMAN

*Attesting Officer*     *Commissioner of Patents and Trademarks*